United States Patent [19]

Penners et al.

[11] Patent Number: 5,651,985
[45] Date of Patent: Jul. 29, 1997

[54] EXPANDABLE PHARMACEUTICAL FORMS

[75] Inventors: Gunther Penners, Leverkusen; Klemens Lustig, Wuppertal; Jörg Petersen-von Gehr, Bochum, all of Germany

[73] Assignee: Bayer Aktiengesellschaft, Leverkusen, Germany

[21] Appl. No.: 392,008

[22] Filed: Feb. 21, 1995

[30] Foreign Application Priority Data

Feb. 28, 1994 [DE] Germany ............ 44 06 424.1

[51] Int. Cl.$^6$ ............ A61K 9/26; A61K 9/58
[52] U.S. Cl. ............ 424/469; 424/466; 424/487
[58] Field of Search ............ 424/486, 501, 424/457, 468, 469, 487; 425/501

[56] References Cited

U.S. PATENT DOCUMENTS

| Re. 27,107 | 3/1971 | Levesque. | |
|---|---|---|---|
| 3,458,622 | 7/1969 | Hill. | |
| 3,574,820 | 4/1971 | Johnson et al.. | |
| 3,634,584 | 1/1972 | Poole. | |
| 3,976,764 | 8/1976 | Watanabe et al.. | |
| 4,101,650 | 7/1978 | Umezawa. | |
| 4,167,558 | 9/1979 | Sheth et al.. | |
| 4,434,153 | 2/1984 | Urquhart et al.. | |
| 4,547,359 | 10/1985 | Zierenberg et al. | 424/468 |
| 4,971,805 | 11/1990 | Kitanishi et al. | 424/494 |
| 5,158,777 | 10/1992 | Abramowitz et al.. | |
| 5,167,964 | 12/1992 | Muhammad et al.. | |

FOREIGN PATENT DOCUMENTS

| 235718 | 9/1987 | European Pat. Off.. |
|---|---|---|
| 250038 | 12/1987 | European Pat. Off.. |
| 326816 | 8/1989 | European Pat. Off.. |
| 9300889 | 1/1993 | WIPO. |

OTHER PUBLICATIONS

Derwent Database, Derwent Abstract 87-099083, abstract of JP 62-48618 (Mar. 3, 1987).
Derwent Database, Derwent Abstract 77-56485y, abstract of JP-52-076418 (Jun. 27, 1977).
Derwent Database, Derwent Abstract 94-178,692, abstract JP 06-24 959 (Feb. 1, 1994).
Derwent Database, Derwent Abstract 88-024371, abstract of JP 62-283919 (Dec. 9, 1987).
Derwent Abstract of JP-03-34,929, (Feb. 14, 1991).
Derwent Abstract of JP-03-34,292, (Feb. 14, 1991).
Derwent Abstract of JP-62-283,919, (Dec. 9, 1987).
Chemical Abstracts, Abstract No. 120:331151f, abstract of JP-06-24,959, (1994).

*Primary Examiner*—Peter F. Kulkosky
*Attorney, Agent, or Firm*—Sprung Horn Kramer & Woods

[57] ABSTRACT

The present invention relates to administration forms having an extended gastric residence time, in the preparation of which mixtures of polymers containing lactam groups and polymers containing carboxyl groups are used, and which are distinguished both by marked swelling properties and by high dimensional stability in the swollen state.

6 Claims, 2 Drawing Sheets

EXPANDABLE PHARMACEUTICAL FORMS

The present invention relates to mixtures of polyvinyllactams and polyacrylates in the preparation of pharmaceutical systems having controlled release of active compound, which are characterized in that they swell strongly in the aqueous environment of the stomach and reside in the stomach for an extended period of time. Optionally, the gastric residence time of the system according to the invention can also be affected by additional incorporation of a gas-forming mixture, as the gas formed reduces the density of the system, by means of which it floats on the stomach contents and thus cannot very easily reach the pylorus, which is located in the lower region of the stomach.

In comparison with the administration of a number of rapidly releasing individual doses at certain intervals, the administration of an individual dose of a medicament from which the active compound is released in a controlled manner over a prolonged period (sustained-release formulation) has the advantage that over a prolonged period a constant and uniform blood level of the active compound is guaranteed. In pharmacy, sustained-release formulations of all sorts of types are known. There are, for example, sustained-release formulations which are based on the controlled erosion of a matrix containing active compound or those from which a water-soluble active compound is released by controlled diffusion through one or more polymer layers surrounding the formulation. In another sustained-release administration form, the controlled release is based on displacement of a layer containing active compound from the osmotically active administration form surrounded by a water-permeable membrane as a result of osmotic water absorption. Pressure equalization or release of active compound in this case takes place through a hole in the membrane.

The sustained-release administration forms briefly described above, however, are only utilizable for active compounds which are absorbed effectively in all regions of the gastrointestinal tract. They are unsuitable for active compounds which on account of their physicochemical properties or due to microbial degradation have so-called absorption windows, i.e. are only absorbed in certain regions of the gastrointestinal tract (GI tract), because they pass through the gastrointestinal tract continuously and their residence time in the absorbing part of the GI tract is thus too short to guarantee a long-term action. Examples of substances whose bioavailability is strongly dependent on the local physiology in the GI tract and which preferably are absorbed in the higher sections of the intestine are ciprofloxacin and nimodipine. Ciprofloxacin is readily soluble in the acidic environment of the stomach. In the intestine, where neutral to slightly alkaline pH conditions prevail, however, precipitation of the active compound occurs, which adversely affects absorption in the lower sections of the intestine. Nimodipine is degraded by the bacterial flora prevailing in the colon, and can therefore only be effectively absorbed in the upper region of the intestine. Further active compounds which have absorption windows in the upper GI tract are captopril and ranitidine. Other active compounds in turn, such as, for example, certain antacids and pepstatin, are locally active and can display their action only if they are released at the site of action, the stomach.

In view of the above explanations, it is clear that a large number of active compounds are unsuitable for conventional sustained-release formulations and that there is a need for systems which reside in the stomach over a relatively long time and release the active compound there in a controlled manner.

Various mixtures which are based on swellable or floatable administration forms are described in the patent literature for prolonging the residence time. Thus U.S. Pat. No. 3,574,820 and U.S. Pat. No. 4,434,153, for example, describe tablets which swell in the stomach and thereby become so large that due to their bulkiness they can no longer pass through the pylorus.

In addition to bulkiness, reduction in density is also used as a measure for prolonging the gastric residence time. Administration forms whose density is lower than that of the stomach content float and are thus kept away from the stomach exit, which is located in the lower region of the stomach. JP 62283919 describes, for example, a tablet comprising a part containing active compound and a part which contains a gas-forming mixture. In contact with aqueous media, carbon dioxide is formed, whereby the average density of the administration form is reduced and the tablet floats on the stomach contents. The reduction of the density by gas formation was also used, as described in EP-A 0235718, with granules of an active compound and a gas-forming mixture coated with a permeable flexible lacquer layer. The abovementioned effects of bulkiness and density reduction due to gas formation are also employed in combination, as shown in Japanese Patent Application 284093/91.

Other administration forms described in the patent literature are not dependent on gas formation for reducion of the density and as a result of their construction already have a density on administration which guarantees the ability to float on the stomach contents. Thus U.S. Pat. No. 3,976,764 describes systems in all types of embodiments which are constructed such that a hollow core, or a core of low density, was coated with a layer containing active compound. Based on this, EP 0326816 describes administration forms in which the reduction of the density is achieved by the use of structural elements having hollow spaces, such as foams or hollow bodies. Administration forms are described in U.S. Pat. No. 4,167,558 which essentially consist of a mixture of active compound and gel-forming polymers in a capsule. A gel body which still contains dry powder mixture is formed in the stomach by swelling of the powder mixture after dissolution of the capsule.

The active compound is released in the course of time by erosion of the gel covering. New gel is in this case formed continuously by further swelling of the dry core. The administration form remains capable of floating until the entire powder mass is soaked through.

Despite the versatility of the mixtures for prolonging the gastric residence time, their conversion to practical pharmaceutical forms is difficult for various reasons. Pure floating pharmaceutical forms such as the pellets presented above (EP-A-0235718) or systems having an inherent low density (U.S. Pat. No. 3,976,764, EP-A-0326816 and U.S. Pat. No. 4,167,558) can only reside in the stomach for a relatively long time if the stomach contains food. In the fasting state, administration forms of this type, due to their relatively small size, leave the stomach within a short time. In addition, the said administration forms having a low inherent density, due to their relatively low active compound content relative to the volume of the total administration form, are only suitable for low-dose active compounds. The granules described in EP 0235718 B1 can in turn only be used for water-soluble active compounds, which greatly restricts their use range.

The swellable tablets described in U.S. Pat. No. 3,574,820, U.S. Pat. No. 4,434,153 and in JP 284093/91 suffer from the properties of the swelling matrix used. A good swelling matrix can absorb many times its original weight of moisture. At the same time, however, it must also have a certain dimensional stability in the swollen state in order to stand up to the mechanical stress to which it is subject in the stomach. Normal linear gel-forming agents such as modified celluloses, polyoxyethylene and polyvinylpyrrolidone (PVP), or alternatively crosslinked polymers, for example based on PVP or polyacrylates, are indeed distinguished by good liquid absorption, but their dimensional stability greatly decreases with increasing degree of swelling because of the poor association between the hydrated linear polymer chains or crosslinked polymer particles, which leads to the erosion or to the dissolution of the gel layer. In JP 284093/91, the administration form was therefore coated with a water-permeable, expandable lacquer. However, this process is complicated and restricts its use to water-soluble active compounds.

Gels which consist, as a tablet, of completely crosslinked polymers, as described in U.S. Pat. No. 3,574,820, have substantially better mechanical properties. Since, however, these crosslinked polymers are new excipients without registration, their use is not foreseeable.

Examples of gels are also known in which the crosslinking leading to the gel formation is not based on covalent bonds, but on physicochemical interactions between various polymers. U.S. Pat. No. 3,634,584 thus describes gels comprising mixtures of carboxyvinyl polymers and polyethylene glycol and U.S. Pat. No. 3,458,622 the use of mixtures of PVP and carboxyvinyl polymers in the preparation of administration forms having controlled release of active compound. The gels described, however, are not distinguished by marked mechanical stability, which already follows from the fact that they are used as an erosion matrix for the controlled release of active compounds. In addition, these gels do not have any marked swelling properties. JP 334292 describes gels comprising polymers containing amide groups and N-substituted lactams as enzyme carrier systems. These gels also cannot be stressed mechanically, as they dissolve in relatively large volumes of aqueous media.

The prior art in general concerns the difficulty of preparing of administration forms having a prolonged gastric residence time and in particular the difficulty of using swellable administration forms based on pharmaceutically acceptable polymers which have a high dimensional stability in the swollen state and due to their bulkiness reside in the stomach for a relatively long time.

The present invention relates to administration forms having a relatively long gastric residence time, in the preparation of which mixtures of polymers containing lactam groups and polymers containing carboxyl groups are used, and which are distinguished both by marked swelling properties and by high dimensional stability in the swollen state.

Figure 1:
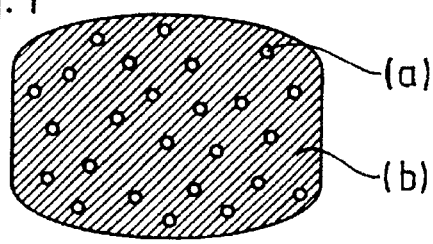
FIGS. 1–4 depict cross-sectional examples of the different enbodiments according to the invention.

It has been found that administration forms which, in addition to active compound (I) and auxiliaries (II) customary in pharmacy, contain mixtures of polymers (III) containing lactam groups and polymers (IV) containing carboxyl groups as gel-forming agents, absorb many times their original weight of water in media having an acidic pH, as is typically present in the stomach, and in contrast to administration forms which contain comparable amounts of a conventional gel-forming agent, swell to give dimensionally stable gels. It is advantageous here if the polymers (III) and (IV) are present in the gel-forming agent in intensively mixed form. The administration forms optionally additionally contain gas-forming agents (V).

The polymers (III) containing lactam groups contained in the gel-forming agent are compounds based on vinyl-lactams such as vinylcaprolactam and vinylpyrrolidone, which are contained in amounts between 20 and 100% by weight, but preferably between 80 and 100% by weight, relative to the vinyl monomers employed in the preparation. Particularly preferred polymers containing lactam groups within the meaning of the invention are linear polyvinylpyrrolidones having a high molecular weight, such as are marketed, for example, by BASF under the trade names "LUVISKOL K 90®" or "KOLLIDON K 90®".

The polymers (IV) containing carboxyl groups contained in the gel-forming agent are both polymers containing titratable carboxyl groups which have an acid number between 50 and 1,200 mg of KOH/g, but preferably between 300 and 1,000 mg of KOH/g of polymer solid substance. The acid number indicates how many mg of KOH are necessary for the neutralization of the acidic groups contained in 1 g of dry polymer substance. Examples of such polymers are carboxymethylcellulose, alginates or synthetic polymers based on vinyl monomers, such as acrylic acid, methacrylic acid, maleic acid or fumaric acid. Particularly preferred polymers containing lactam groups within the meaning of the invention are acrylic resins containing carboxyl groups, such as are marketed by Röhm Pharma GmbH under the trade name "EUDRAGIT®". Particularly preferred Eudragit grades are "EUDRAGIT L®" and "EUDRAGIT S®".

The polymers (III) containing lactam groups and the polymers (IV) containing carboxyl groups are present in the administration forms according to the invention in a mixing ratio of between 40:60 and 98:2, but preferably between 80:20 and 95:5. The swelling properties of the administration forms, and also their mechanical stability in the swollen state, is in this case affected substantially by the mixing ratio of the two polymers.

The intensive mixing of the polymers (III) and (IV), which in the end essentially determines the good swelling properties and the mechanical stability of the administration forms prepared therefrom, can be guaranteed, for example, by drying mixed solutions which contain the polymers according to the invention. In this process, the polymer containing carboxyl groups is present in its neutralized form in order to avoid gel formation in the mixed solution. In another method for the preparation of polymer mixtures, a powder mixture of the polymers, optionally provided with active compound and/or other auxiliaries customary in pharmaceutical technology, such as lubricants, binders, fillers etc., is processed by means of suitable methods, e.g. tabletting, to give shaped articles of desired geometry, and then stored for a relatively long time at a temperature which should at least be above the glass transition temperature of one of the polymers. This storage causes an intensive molecular association due to interpenetration of the various polymers.

Auxiliaries (II) within the meaning of the invention are those which are necessary to guarantee the preparability of the administration forms or their properties such as hardness, abrasion etc. Among these are, for example, the flow enhancers, fillers, lubricants and binders customary in pharmaceutical practice and known to the expert.

Suitable active compounds or active compound combinations (I) according to the present invention are all those which are suitable for oral administration and for sustained-release therapy. The prerequisite, however, is that they are not acid-sensitive active compounds. The administration forms according to the invention are particularly suitable for active compounds which display their absorption window in the stomach or in the upper part of the gastrointestinal tract, such as ciprofloxacin, nimodipin, captopril and ranitidine, or else display their action there locally, such as certain antacids. Examples of such antacids are magnesium hydroxide and magnesium trisilicate.

Suitable gas-forming agents (V) which can optionally be employed to increase the buoyancy are all substances which, in contact with water or gastric fluid, are able to form non-toxic gases. Examples are hydrogen carbonates such as, for example, sodium hydrogen carbonate, which are employed individually, or in combination with acids. Examples of such acids are citric acid or alternatively polyacrylates such as are marketed by B. F. Goodrich Chemical GmbH under the name "CARBOPOL®". The gas which forms is incorporated into the hydrated gel layer as bubbles and thus contributes to the buoyancy of the tablet.

The ratios of the amounts of gel-forming agent (III) and (IV) contained in the administration forms according to the invention to active compound (I) or auxiliaries (II) are subject to no restrictions. They depend on the dosage of active compound, the nature of the active compound and the construction of the administration form. It is essential, however, for the administration form to contain sufficient gel-forming agent so that after administration it can swell up to a size which prevents passage through the pylorus for a relatively long time.

Likewise, the amount of active compound contained in the administration forms according to the invention can also be very different, depending on the nature of the active compound, the degree of delay of release of the active compound desired and the type of construction of the administration form.

The administration forms according to the invention can be prepared in very different embodiments such as tablets, capsules and granules or pellets. The tablet embodiment, however, is particularly advantageous. The active compound, for example, can thus be compressed together with the polymers according to the invention and optionally other auxiliaries customary in pharmaceutical technology to give a homogeneous tablet. Systems in a form in which the active compound and the polymers (III) and (IV) are present spatially separated from one another are particularly preferred, however, as is the case, for example, in core-coated tablets having an acentric core exposed on one surface and also in double-layer tablets. A gas-forming mixture can optionally also be incorporated in the administration forms in order to assist the prolongation of the residence time in the stomach due to swelling by means of additional buoyancy.

FIGS. 1 to 4 show, represented schematically as a cross-sectional drawing, examples of different embodiments of the administration forms according to the invention. FIG. 1 shows an administration form in which the active compound (a) is dissolved in molecular form, or else is incorporated in disperse form in a gel-forming agent (b) based on mixtures of polymers (III) containing lactam groups and polymers (IV) containing carboxyl groups. The gel-forming agent in the types of construction shown and mentioned below can contain gas-forming agents (V) additionally to the active compound. In the administration form shown in FIG. 2, the gel-forming swellable layer (c) and the layer (d) containing the active compound are present separately from one another, in the form of a double-layer tablet. As shown by way of example in FIGS. 3 and 4, a spatial separation of the two layers can also be achieved using other embodiments. Depending on the solubility of the active compound, one or the other embodiment is to be preferred. An administration form according to FIG. 1 is thus particularly suitable for gastric juice-soluble active compounds, and the other embodiments are better suited to insoluble active compounds. It is common to all embodiments, however, that they swell strongly in the stomach and, as a result, reside in the stomach for a relatively long time.

The following examples illustrate the invention.

EXAMPLE 1

Preparation of the gel-forming agent and the swelling body: Solutions of the polyvinylpyrrolidone Luviskol K 90® (polymer containing lactam groups) and Eudragit L®, a copolymer based on methacrylic acid and methyl methacrylate (polymer containing carboxyl groups), served as a basis for the preparation of the gel-forming agent. 950 g of a 17.5% strength by weight solution of Luviskol K 90® in water were mixed with 50 g of a 17.5% strength aqueous solution of Eudragit L® adjusted to pH 7 with ammonia. The mixed solution was freeze-dried, and the lyophilisate obtained was ground and sieved to 500 micrometres. Tablets having a weight of 400 mg and a diameter of 12 mm were produced from this material by means of a customary eccentric press at a press force of 10 kN.

Determination of the swelling behaviour: The tablets were incubated in 0.1 N HCl at a temperature of 37° C. The tablets were removed from the incubation medium at specific times, the adhering liquid was removed and the weight of the swollen tablets was determined. The degree of swelling (Qt) at the time t was defined as the quotient of the weight of the tablets at the time t (Wt) and the dry weight of the tablet (Wo):

$$Qt = wt/wo$$

Figure 5:
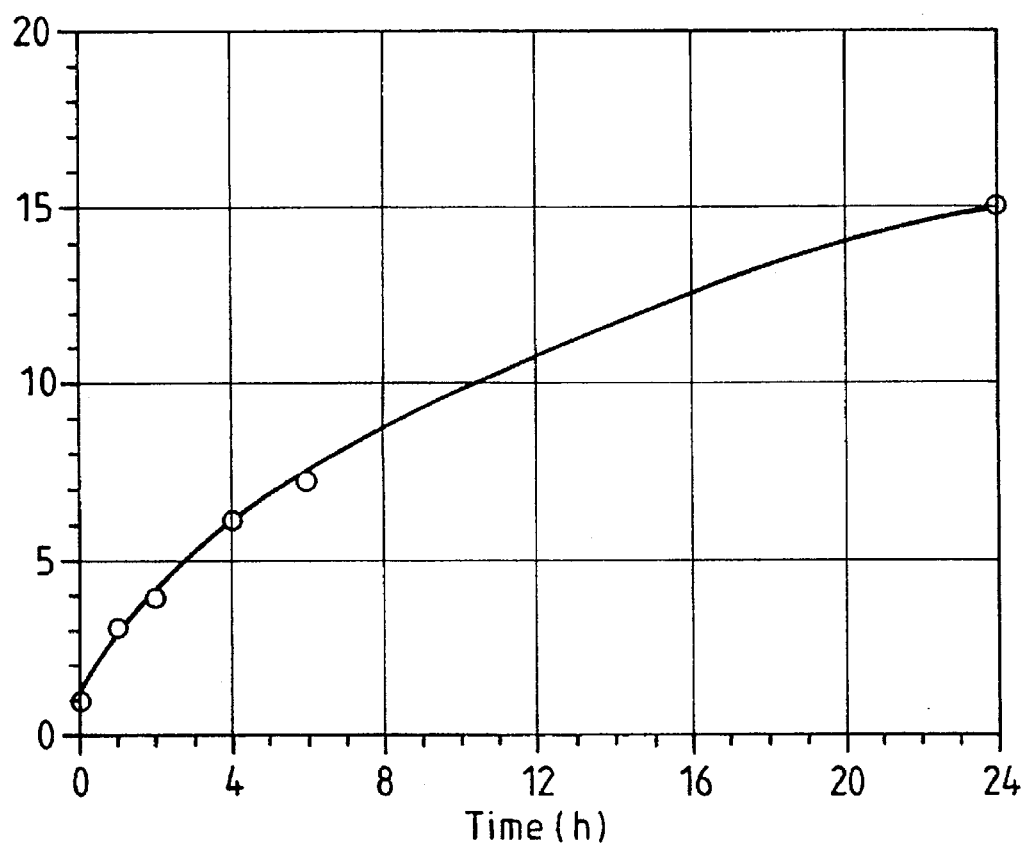
FIG. 5 depicts graphically the degree of swelling as a function of time.

The course of the degree of swelling of the tablet described as a function of time is shown graphically in FIG. 5.

Determination of the mechanical properties: Stable gels are distinguished in that although they increase in volume during the swelling process, they retain their original shape during the course of this (dimensional stability). In addition, they react to mechanical deformation in a reversible manner, and reassume their original shape after the deforming force is taken away (high elasticity). Gels of the composition described are distinguished by high dimensional stability and good elastic behaviour.

COMPARISON EXAMPLE 2

Tablets were prepared having the same composition as in Example 1, the gel-forming components not being processed as a molecular mixture, prepared by means of solutions, however, but as a pure powder mixture. The tablets had poor mechanical properties in 0.1 N HCl. They were strongly sensitive to erosion and dissolved completely in the course of time. A determination of the degree of swelling (Qt) as a function of time, according to Example 1, was not possible because of the inadequate mechanical strength.

EXAMPLE 3

Tablets containing different ratios of Luviskol K 90® and Eudragit L® were prepared according to Example 1 and their degree of swelling (Qt) was determined after 24 hours according to Example 1. The results are summarized in the following table.

| Weight ratio Luviskol K. 90 ®: Eudragit L ® | Degree of swelling Qt after 24 hours |
| --- | --- |
| 90:10 | 10.4 |
| 92.5:7.5 | 12.7 |
| 95:5 | 15.3 |
| 96:4 | 17.2 |
| 97:3 | 18.2 |
| 98:2 | 20.4 |
| 100:0 | * |

*)No gel formation, tablet dissolves completely.

From these data it is evident that the swelling behaviour of the gels can be controlled by the ratio Luviskol K 90®:Eudragit L®. With increasing Eudragit L® content, the gels have an increasing dimensional stability and elasticity. Gels are only formed if both polymeric components are present. Pure PVP is not a stable gel-forming agent.

COMPARISON EXAMPLE 4

From the known gel-forming agents listed in the following table, tablets with the same weight and dimensions as in Example 1 were pressed and their degree of swelling (Qt) was determined after 24 hours according to Example 1.

| Polymer | Type | Manufacturer | Degree of swelling (Qt) after 24 hours |
| --- | --- | --- | --- |
| Polyoxyethylene | Polyox Coagulant ® | Union Carbide | 11.7 |
| Carboxymethyl-cellulose | Tylose c 6000 ® | Hoechst | * |
| Hydroxyethyl-cellulose | Tylose H 10,000 ® | Hoechst | 10.3 |
| Polyacrylate | Carbopol 974 p ® | B. F. Goodrich | 9.4 |

*)Tablet disintegrates within one hour

The gel-forming agents mentioned all have poor mechanical properties. They are strongly sensitive to erosion and are deformed irreversibly even with low mechanical stress. On the other hand, the gels described in Example 3 are insensitive to erosion with comparable, or better, swelling behaviour (e.g. gels based on 92.5 parts of PVP K 90 and 7.5 parts of Eudragit L) and exhibit no lasting deformation on mechanical stress due to their high elasticity.

EXAMPLE 5

Preparation of a monolayer tablet according to FIG. 1: 12 mm tablets of the following composition were prepared in an eccentric press at a press force of 10 kN:

| Substance used | Amount (mg/tablet) |
| --- | --- |
| Ciprofloxacin-HCl | 250 |
| Gel mixture prepared according to Example 1 (Luviskol K 90 ®: Eudragit L ® = 95:5) | 229.8 |
| Sodium bicarbonate powder | 20.2 |

The release of active compound from the tablets was determined in a customary release apparatus. In the course of 24 hours the tablets released the active compound completely in 900 ml of 0.1 N HCl at 37° C. with continuous stirring (75 revolutions per minute). During the course of this they absorbed so much liquid that their diameter was 3 cm with good mechanical stability according to the criteria mentioned in Example 1.

EXAMPLE 6

Figure 2:
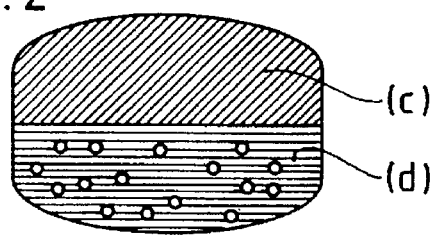
Figure 3:
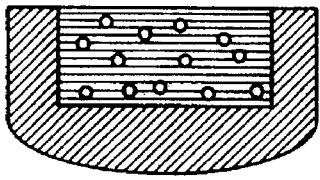
Figure 4:
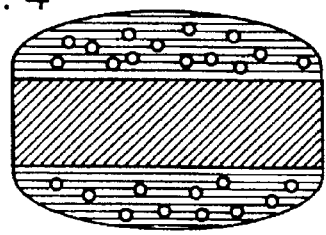

Preparation of a double-layer tablet according to FIG. 2: Double-layer tablets having a diameter of 12 mm, consisting of a swelling layer and an active compound-containing layer, were prepared by the recipe shown below by pressing in an eccentric press at a press pressure of 1.5 tons:

The release of active compound from the tablets was determined in a customary release apparatus. In the course of 7 hours the tablets released 90% of the active compound linearly in 900 ml of 0.1 N HCl at 37° C. with continuous stirring (75 revolutions per minute). The active compound-containing layer dissolved almost completely during the course of this. The swelling layer, on the other hand, increased greatly in volume in the course of time. The diameter was 2 cm after 6 hours and 3 cm after 24 hours. The gel layer was distinguished by good mechanical properties even after 24 hours. It was reversibly deformable on mechanical stress and exhibited no visible erosion. As a result of gas formation due to the sodium bicarbonate contained in the gel layer, the tablet drifted to the surface of the release medium during the release.

| Substance used | Amount (mg/tablet) |
| --- | --- |
| Swelling layer | |
| Gel mixture prepared according to Example 1 (Luviskol K 90 ®: Eudragit L ® = 95:5) | 340 |
| Carbopol 974 P | 34 |
| Magnesium stearate | 10 |
| Red iron oxide | 2.5 |
| Sodium bicarbonate | 34 |
| Active compound-containing layer | |
| Ciprofloxacin HCl | 250 |
| Magnesium stearate | 2.9 |
| Klucel JF ® (hydroxypropylcellulose) | 80 |

We claim:

1. A pharmacologically active composition in a physical form imparting a prolonged gastric residence time, said physical form being selected from the group consisting of tablets, capsules, granules and pellets, said composition comprising:

(I) at least one pharmacologically active compound, (II) at least one pharmacologically acceptable auxiliary, (III) polyvinylpyrrolidone, (IV) a methacrylic acid polymer having an acidic number between 100 and 1,200 mg of KOH/g of polymer solid substance, and (V) optionally a gas-forming additive, the polymers (III) and (IV) being present in the form of a homogeneous mixture on the molecular level, the mixture being present in 30–90% by weight of the composition, the weight ratio of (III):(IV) ranging from 80:20 to 95:5, and the composition in dry compressed state being able to absorb many times its weight of acidic water thereby to form a highly swollen gel of high mechanical and dimensional stability capable of improved prolonged release of the pharmacologically active compound.

2. A tablet according to claim 1, wherein the active compound (I) comprises at least one compound selected from the group consisting of ciprofloxacin, nimodipine, captopril, ranitidine, cyclosporin, baclofen, allopurinol, furosemide, cefoxitine, 5-aminosalicylate and moexipril, and the polymer (IV) is a copolymer of methacrylic acid and methyl methacrylate having a ratio of free carboxyl groups:ester groups from 1:1 to 1:2.

3. A tablet according to claim 1, wherein the active compound (I) is an antacid and the polymer (IV) is a copolymer of methacrylic acid and methyl methacrylate having a ratio of free carboxyl groups:ester groups from 1:1 to 1:2.

4. A tablet according to claim 1, wherein the active compound (I) comprises at least one of magnesium hydroxide and magnesium trisilicate, and the polymer (IV) is a copolymer of methacrylic acid and methyl methacrylate having a ratio of free carboxyl groups:ester groups from 1:1 to 1:2.

5. A tablet according to claim 1, wherein the active compound (I) comprises at least one of magnesium hydroxide and magnesium trisilicate.

6. A tablet according to claim 1, wherein the active compound (I) comprises ciprofloxacin and the polymer (IV) is a copolymer of methacrylic acid and methyl methacrylate having a ratio of free carboxyl groups:ester groups from 1:1 to 1:2.

* * * * *